July 17, 1956 G. M. REED Plant Pat. 1,497
WEEPING CRABAPPLE TREE
Filed Jan. 5, 1953
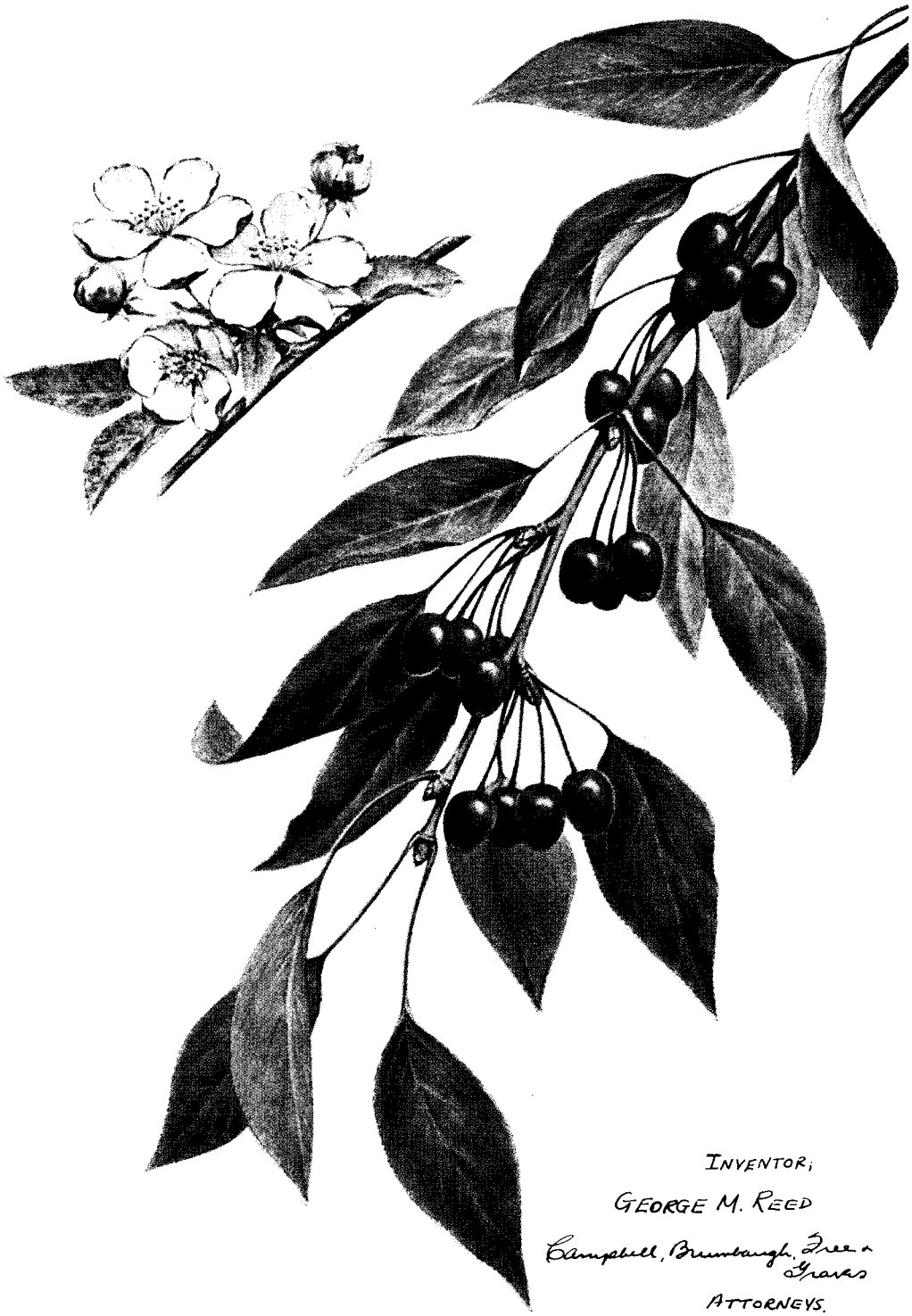
INVENTOR;
GEORGE M. REED
Campbell, Brumbaugh, Free & Graves
ATTORNEYS.

United States Patent Office

Plant Pat. 1,497
Patented July 17, 1956

1,497

WEEPING CRABAPPLE TREE

George M. Reed, Pittsburgh, Pa., assignor to The Brooklyn Institute of Arts and Sciences, Brooklyn, N. Y., a corporation of New York Application January 5, 1953, Serial No. 329,757

1 Claim. (Cl. 47—62)

The present invention relates to plant varieties involving trees of the crabapple type, which exhibit flowering and weeping characteristics, and embodies more specifically a flowering crabapple tree of strongly weeping habit having small bright-red fruits and having the characteristics of strength and vigor.

Varieties of weeping crabapple trees now known are characterized generally by weakness and not being strongly weeping in nature, and it is an object of this invention to provide a weeping crabapple tree of striking appearance and beauty, having not only a strongly weeping habit, but also being a tree of strength and vigor with quantities of beautiful fruits borne on drooping branches and retained thereon until very late in the fall.

The tree of my invention is exhibited in the accompanying drawing, which is a reproduction in color showing such a tree with the fruits thereon.

The seedling of the weeping crabapple tree of my invention is characterized in habit as attaining in fourteen years of age, a height of about four meters, with a short trunk and a rounded crown of about three meters in diameter, the bark being smooth and gray-brown.

The buds of the tree are slender and pointed, being approximately 3.5 to 5.5 millimeters long with light brown to chestnut scales having darker and somewhat ciliate margins, while the branchlets are very long, slender and pendulous, often reaching the ground.

The leaves of my new tree are narrowly to broadly elliptical and average from approximately 6 to 12.5 centimeters long to approximately 3 to 6 centimeters broad, being somewhat pubescent ventrally and slightly pubescent along the mid-rib dorsally. The apices of the leaves taper or are abruptly acuminate, while the bases vary from obtuse to narrowly round. The leaf margins are irregularly to doubly serrate, averaging from approximately five to six teeth per centimeter, the teeth varying from obtuse to acuminate. The petioles are pubescent, ranging from approximately 2.4 to 5.5 centimeters long and sometimes slightly winged with or without stipules which, if present, are linear, stipitate and hairy, being approximately 1 to 2 millimeters long.

The flowers of the new weeping crabapple tree occur in umbels of 4 to 6 on apices of short, leafy stems, frequently with a secondary umbel of from 3 to 4 flowers arising from the axil of a leaf below the inflorescence, with the pedicels 1.5 to 3 centimeters long, and slender, glabrous with one or two linear brown scales near the base. The buds are deep pink, the flowers white and from 2.5 to 4 centimeters across, the sepals ranging from spreading to slightly reflexed, lanceolate, acute, glabrous outside, woolly pubescent inside, and ranging from approximately 4.5 to 6 millimeters in length to approximately 1.5 to 3 millimeters in breadth. The petals are white ventrally, blush-pink dorsally, irregularly oval, spurred with rounded to emarginate apices, and range from approximately 1.8 to 2.2 centimeters in length to approximately 1.2 to 1.5 centimeters in breadth. There are 16, 18, or 20 short stamens, the anthers buff-yellow, and there are 4 light-green styles exceeding the stamens by .8 to 1 centimeter.

The fruit of the tree is borne in great profusion every year and is currant-red (Royal Horticultural Society Color Chart No. 821/1), oblong and tapering, being from approximately 1.2 to 1.7 centimeters long by approximately 1 to 1.5 centimeters in diameter on pedicels approximately 2 to 4.5 centimeters long. The seeds are light brown, indistinctly longitudinally striate, obovoid, more or less pointed at hylar end, and range from approximately 4.5 to 5 millimeters in length to approximately 2 to 3 millimeters in breadth.

The leaves fall very early in the fall while the fruit remains until very late, causing the tree to be very beautiful with quantities of small bright currant-red fruits borne on drooping branches.

The tree differs from other weeping crabapple trees in its strongly weeping form, green foliage, white flowers, and long persistent, bright red fruits borne in profusion yearly, being produced from hybridization and selections from its antecedent "Excellenz Thiel," which is its only known antecedent. As far as is known, "Excellenz Thiel" was introduced in 1909 by Ludwig Spaeth of Berlin, Germany, and was brought to this country by the Arnold Arboretum in 1912, and is not patented.

The weeping crabapple tree of this invention differs from its antecedent "Excellenz Thiel" in that it is strong and vigorous, with a strongly weeping habit, and having small bright-red fruits, whereas the "Excellenz Thiel" is a weak tree, only partially weeping in habit, and has relatively larger and yellow fruits.

The tree of the present invention was asexually reproduced by the applicant, George M. Reed, by budding at the Brooklyn Botanic Garden, 1000 Washington Avenue, Brooklyn 25, New York, from a seedling of "Excellenz Thiel" selected and grown at said Brooklyn Botanic Garden by the applicant.

I claim:

The new and distinct variety of crabapple tree as herein described and illustrated characterized by a strongly weeping characteristic and small bright-red fruits.

No references cited.